US 6,713,615 B2

(12) United States Patent
Kashimura et al.

(10) Patent No.: US 6,713,615 B2
(45) Date of Patent: Mar. 30, 2004

(54) PROCESS FOR PRODUCING ERYTHROMYCIN DERIVATIVE

(75) Inventors: Masato Kashimura, Tokyo (JP); Hiroaki Kamiyama, Tokyo (JP); Takeshi Kuwada, Tokyo (JP); Nobuyuki Suzuki, Tokyo (JP); Takashi Adachi, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/344,529

(22) PCT Filed: Aug. 10, 2001

(86) PCT No.: PCT/JP01/06928

§ 371 (c)(1),
(2), (4) Date: Feb. 12, 2003

(87) PCT Pub. No.: WO02/14339

PCT Pub. Date: Feb. 21, 2002

(65) Prior Publication Data

US 2003/0191295 A1 Oct. 9, 2003

(30) Foreign Application Priority Data

Aug. 14, 2000 (JP) .......................................... 2000-245850

(51) Int. Cl.[7] .......................... C07H 1/00; C07H 17/08

(52) U.S. Cl. .......................... 536/7.4; 536/7.2; 536/7.3; 536/18.5

(58) Field of Search .......................... 536/7.2, 7.3, 7.4, 536/18.5

(56) References Cited

FOREIGN PATENT DOCUMENTS

| JP | 2001-72699 | 3/2001 |
|---|---|---|
| WO | WO 99/11651 | 3/1999 |
| WO | WO 99/16779 | 4/1999 |
| WO | WO 00/78773 | 12/2000 |

OTHER PUBLICATIONS

International Search Report of PCT/JP01/06928 dated Nov. 13, 2001.

*Primary Examiner*—Elli Peselev
(74) *Attorney, Agent, or Firm*—Sughrue Mion, PLLC

(57) ABSTRACT

There is provided a preparation process useful for an efficient synthesis of 6-O-substituted ketolide derivatives by combining a characterized step of introduction of a substituent at the 6-position by selective cleavage of a C—O bond of the cyclic acetal at the 9-position side via 6,9-cyclic acetal 5-O-desosaminyl erythronolide derivative, a step of conversion into carbonyl groups at the 9- and 3-positions, and a step of 11,12-cyclic carbamation to lead to 6-O-substituted ketolide derivatives.

7 Claims, No Drawings

PROCESS FOR PRODUCING ERYTHROMYCIN DERIVATIVE

TECHNICAL FIELD PERTINENT TO THE INVENTION

The present invention relates to processes for preparing erythromycin derivatives and to intermediates thereof, and particularly relates to a process for preparing 6-O-substituted ketolide derivatives starting from erythromycin and to intermediates thereof.

PRIOR ART

Macrolide antibiotics including erythromycin A have a strong antibacterial activity against Gram-positive bacteria, some Gram-negative bacteria, Mycoplasmas and the like, and have been widely used as agents for the treatment of infections caused by these bacteria. Furthermore, many erythromycin derivatives have been synthesized for the purpose of the improvement of pharmacokinetic properties of erythromycin A, and some of them have already been clinically used as excellent antibiotics. For example, clarithromycin (6-O-methylerythromycin A, U.S. Pat. No. 4,331,803) has been widely used as a therapeutic agent of respiratory tract infections due to its excellent biological properties. There has been recently reported the derivatives which are generically called ketolides and have a potent antibacterial activity against macrolide-resistant bacteria. The structural features of these derivatives are such that the cladinose group at the 3-position of erythromycin A has been removed, and converted into a carbonyl group, the hydroxyl group at the 6-position has been alkylated, and the hydroxyl groups at the 11- and 12-postions have been converted into a cyclic carbamate. Among these ketolides, there is 3-deoxy-3-oxo-6-O-((3-quinol-3-yl)prop-2-enyl)-5-O-desosaminyl erythronolide A 11,12-cyclic carbamate (U.S. Pat. No. 5,866,549, and J. Medicinal Chemistry, vol. 43, pp.1045–1049 (2000)), which has a strong antibacterial activity against both of macrolide-sensitive and macrolide-resistant bacteria that cause respiratory tract infections. As mentioned above, this compound is prepared by modifying at three positions, i.e., at the 6-, 3- and 11,12-positions. The preparation process reported is carried out by once converting the carbonyl group at the 9-position into an oxime derivative, modifying at the 6-position and reproducing a carbonyl group at the 9-position, therefore this manufacturing process needs many steps, and is complicated.

Problems to be Solved by the Invention

An object of the present invention is to provide processes for preparing erythromycin derivatives and intermediates thereof, and more particularly to provide preparation processes useful for an efficient synthesis of a 6-O-substituted ketolide derivative.

Means for Solving the Problems

As a result of diligently studies, the present inventors have found a process for leading to a 6-O-substituted ketolide derivatives, which comprises combining a characterized step of introduction of a substituent at the 6-position by selective cleavage of the C—O bond of the cyclic acetal at the 9-position side via a 6,9-cyclic acetal 5-O-desosaminyl erythronolide derivative, a step of conversion into carbonyl groups at the 9- and 3-positions, and a step of 11,12-cyclic carbamation, thereby the present invention have been accomplished. Specifically, this process is useful as a process for the synthesis of 3-deoxy-3-oxo-6-O-((3-quinol-3-yl)prop-2-enyl)-5-O-desosaminyl erythronolide A 11,12-cyclic carbamate which has been recently reported to have a potent antibacterial activity, and the like.

That is, the present invention is directed to a process for preparing Compound (V) defined below, which comprises the steps of:

(A) providing Compound (I) of the formula:

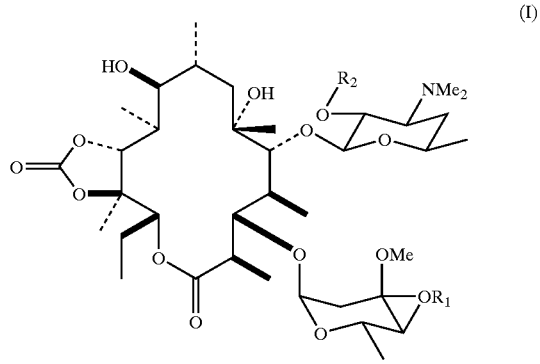

(I)

wherein $R_1$ and $R_2$, which may be the same or different, are a hydrogen atom, formula —CO—$R_A$ wherein $R_A$ is a $C_{1-3}$ alkyl group, $C_{1-3}$ alkyl group substituted with 1–3 halogen atoms, $C_{1-3}$ alkoxy group, phenyl group, phenyloxy group, benzyloxy group, or phenyl group substituted with 1–3 atoms/substituents selected from the group consisting of $C_{1-3}$ alkyl group, $C_{1-3}$ alkoxy group, nitro group, cyano group, halogen atom, acetyl group, phenyl group and hydroxy group, or a silyl group substituted with 2–3 substituents selected from the group consisting of $C_{1-4}$ alkyl group, phenyl group and benzyl group, by reaction of erythromycin with ethylene carbonate, subsequent reduction of ketone in 9-position, and optional protection of hydroxy groups in 2'- and/or 4"-positions, (B) reacting Compound (I) with a compound of the formula:

(1)

wherein A is CH=CH or C≡C; $R_5$ and $R_6$, which may be the same or different, are a $C_{1-7}$ alkyl group, and optionally protecting a resulting 3-hydroxy group, to obtain Compound (II) of the formula:

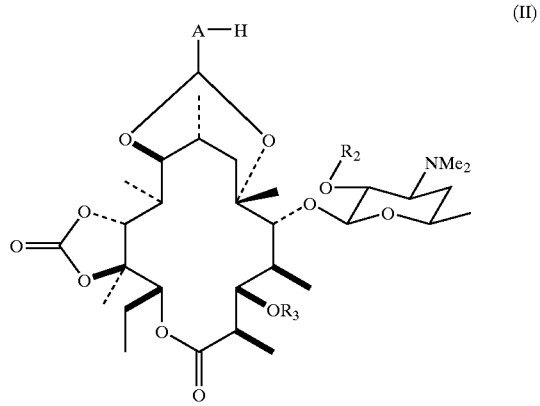

(II)

wherein $R_3$ is the same as $R_1$ defined above; $R_2$ and A are as defined above, (C) reacting Compound (II) with a compound of the formula:

$$X—R_4 \quad (2)$$

wherein X is a halogen atom; $R_4$ is the formula:

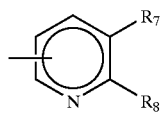

wherein $R_7$ and $R_8$ are a hydrogen atom or, alternatively, they form a benzene nucleus together with adjacent carbon atoms, or the formula:

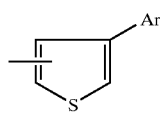

wherein Ar is a pyridyl group, quinolyl group or aryl group, to obtain Compound (III) of the formula:

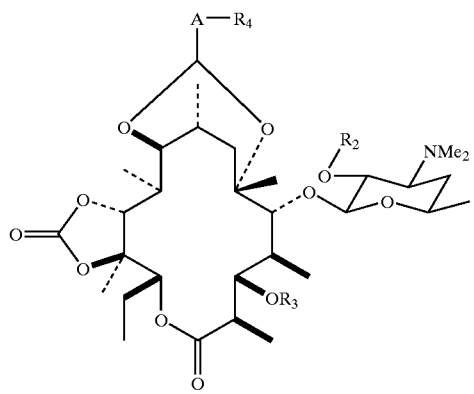

wherein A, $R_2$, $R_3$ and $R_4$ are as defined above, (D) reacting Compound (III) with a compound of the formula:

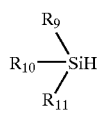

$$(3)$$

wherein $R_9$ is a hydrogen atom, chlorine atom, linear or branched $C_{1-4}$ alkyl group, $C_{1-3}$ alkoxy group, phenyl or benzyl group; $R_{10}$ and $R_{11}$, which may be the same or different, are a chlorine atom, linear or branched $C_{1-4}$ alkyl group, $C_{1-3}$ alkoxy group, phenyl group or benzyl group, to obtain Compound (IV) of the formula:

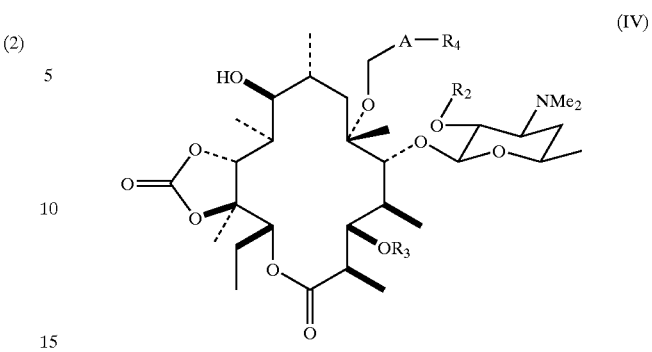

wherein A, $R_2$, $R_3$ and $R_4$ are as defined above, and (E) subjecting Compound (IV) to carbonylation at 9-position, carboxylation at 3-position, 11,12-cyclic carbamation and deprotection of 2'-hydroxy group, to obtain Compound (V) of the formula:

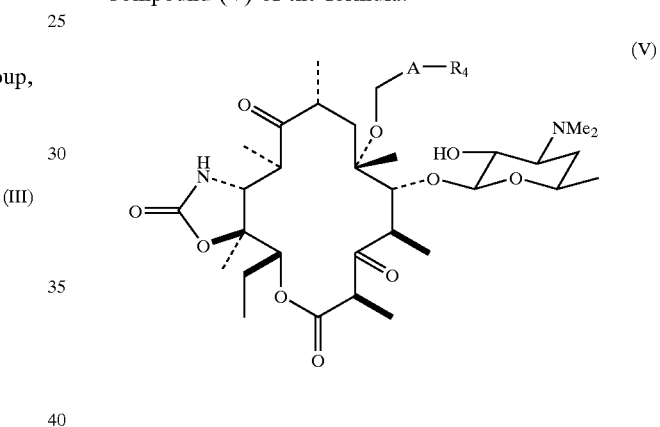

wherein A and $R_4$ are as defined above.

MODE FOR CARRYING OUT THE INVENTION

The present invention is illustrated in more detail as follows.

In the present invention, the term "$C_{1-7}$ alkyl group" refers to linear or branched alkyl groups, which include methyl group, ethyl group, propyl group, isopropyl group, butyl group, t-butyl group, pentyl group, hexyl group and heptyl group. The term "$C_{1-3}$ alkoxy group" refers to methoxy, ethoxy and propoxy groups. The term "halogen atom" refers to fluorine, chlorine, bromine, iodine atom and the like.

The present invention relates to a process for preparing Compound (V) from erythromycin A as a starting material, for example, according to the following reaction scheme, and to intermediates thereof.

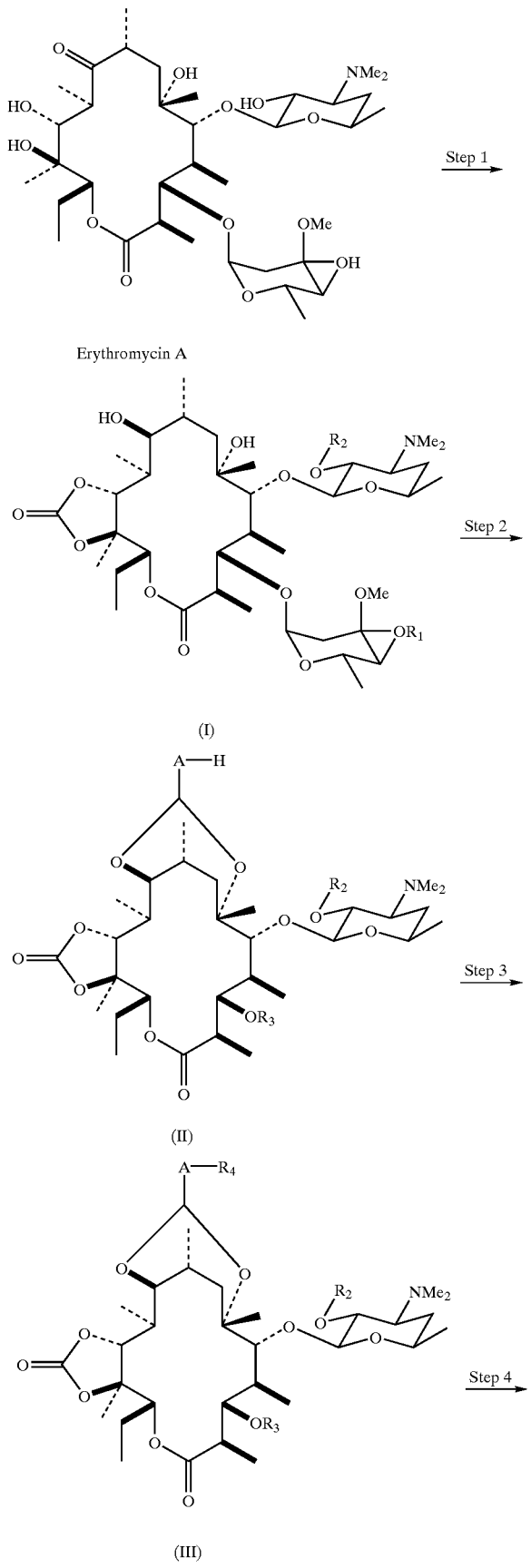

wherein A and $R_1$ through $R_4$ are as defined above, and more particularly, A is CH=CH or C≡C, $R_1$ is hydrogen atom, an acetyl group, a propionyl group, a benzoyl group, a trimethylsilyl group or a triethylsilyl group, $R_2$ is hydrogen atom, an acetyl group, a propionyl group, a benzoyl group, a trimethylsilyl group, a triethylsilyl group or a t-butyldimethylsilyl group, $R_3$ is hydrogen atom, an acetyl group, a propionyl group, a benzoyl group, trimethylsilyl group or a triethylsilyl group, and $R_4$ is a pyridyl group, a quinolyl group, a pyridylthienyl group or a pyridylimidazolyl group.

Step 1. Compound (I) can be prepared according to a method described in WO9813373. That is, erythromycin A is reacted with ethylene carbonate in the presence of a base in an inert solvent to give an erythromycin A 11,12-cyclic carbonate compound. Here, the inert solvent includes diethyl ether, ethyl acetate, dichloromethane, chloroform, acetone, N,N-dimethylformamide, toluene, tetrahydrofuran and a mixture thereof. The base includes sodium carbonate, potassium carbonate, cesium carbonate and pyridine. Next, the carbonyl group at the 9-position is reduced into a hydroxyl group by a reducing agent in an organic solvent, thereby 9-deoxo-9-hydroxyerythromycin A 11,12-cyclic carbonate can be obtained. The organic solvent used herein includes methanol, ethanol, isopropanol, propanol, tetrahydrofuran and N,N-dimethylformamide. The reducing agent includes lithium borohydride, potassium borohydride, sodium cyanoborohydride and sodium borohydride. The hydroxyl group at the 2'-position is then protected with an acetyl, propionyl, benzoyl, trimethylsilyl, triethylsilyl, t-butyldimethylsilyl group or the like to obtain Compound (I). In order to accelerate the reaction, a base can be added for the acylation, and a salt with an acid can be added for the silylation. Examples of the base to be used are N,N-dimethylaminopyridine, pyridine, triethylamine, imidazole, sodium bicarbonate and potassium carbonate. Examples of the salt with an acid to be used are pyridine hydrochloride and ammonium chloride.

Step 2. Compound (I) obtained in Step 1 can be heated together with a compound of the formula:

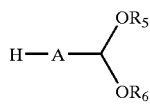

(1)

wherein $R_5$ and $R_6$ are as defined above, in an inert solvent in the presence of an acidic catalyst to obtain a decladinosylated 6,9-cyclic acetal compound (II). Here, the inert solvent includes dichloromethane, chloroform, dichloroethane, chlorobenzene, dichlorobenzene, toluene, xylene, etc. The acidic catalyst to be used includes pyridinium p-toluenesulfonate, pyridine hydrochloride, 3-pyridinesulfonic acid, trimethylamine hydrochloride, triethylamine hydrochloride, etc, and is preferably, pyridinium p-toluenesulfonate. Examples of the compound of formula (1) to be used are acrolein dimethyl acetal, acrolein diethyl acetal, acrolein di-n-propyl acetal, acrolein diisopropyl acetal, acrolein di-n-butyl acetal, acrolein diisobutyl acetal, propiolaldehyde dimethyl acetal, propiolaldehyde diethyl acetal, propiolaldehyde di-n-propyl acetal, propiolaldehyde diisopropyl acetal, propiolaldehyde di-n-butyl acetal, propiolaldehyde diisobutyl acetal, etc.

Step 3. Compound (II) obtained in Step 2 can be reacted with a compound of the formula:

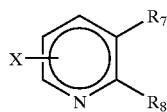

(2)

in which $R_7$, $R_8$ and X are as defined above, or a compound of the formula:

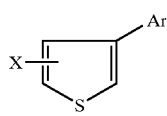

(3)

in which Ar and X are as defined above, in an inert solvent in the presence of, for example, a palladium catalyst to obtain Compound (III). In this case, copper iodide and phosphine may be optionally added. The inert solvent includes toluene, tetrahydrofuran, dioxane, dimethoxyethane and N,N-dimethylformamide, and preferably toluene, tetrahydrofuran and N,N-dimethylformamide. The compound of formula (2) includes quinolyl chloride, pyridyl chloride, quinolyl bromide and pyridyl bromide and the compound of formula (3) includes pyridylthienyl chloride and pyridylthienyl bromide, and of these compounds, quinolyl bromide, pyridyl bromide and pyridylthienyl bromide are preferable.

Step 4. Compound (III) can be reacted with a compound of the formula:

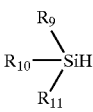

(6)

wherein $R_9$, $R_{10}$ and $R_{11}$ are as defined above, in an organic solvent in the presence of an activating agent such as a Lewis acid to obtain Compound (IV). Here, the organic solvent includes nitrobenzene, nitrotoluene, trichlorotoluene, benzonitrile and methylbenzoate, and preferably nitrobenzene and nitrotoluene. Here, the compound of formula (6) includes trimethylsilane, triethylsilane, trichlorosilane, phenyldimethylsilane, diphenylsilane, triphenylsilane, triethoxysilane, diethylsilane and t-butyldimethylsilane, and preferably triethylsilane and t-butyldimethylsilane. The activating agent to be used includes a Lewis acid (e.g., titanium tetrachloride, aluminum chloride, zirconium tetrachloride, tin tetrachloride, ferric trichloride, zinc chloride and trifluoroboran etherate), trifluoromethane sulfonate and Nafion (registered trademark), and preferably titanium tetrachloride.

Step 5. Compound (IV) wherein $R_3$ is a hydrogen atom can be subjected to a reaction using a sulfur compound such as dimethyl sulfoxide (DMSO) and dimethyl sulfide (Me$_2$S) and an activating agent such as acetic anhydride (Ac$_2$O), N-chlorosuccinimide (NCS) or oxalyl chloride, whereby the hydroxy groups at the 3- and 9-positions are simultaneously oxidized to form a 3,9-dioxo compound, which is then led to 12-O-imidazolyl carbonyl compound using N,N'-carbonyldiimidazole and a base. Subsequently, ammonolysis using ammonia gas and intramolecular Michael addition reaction can lead to a 11,12-cyclic carbamate compound to obtain Compound (V). In this case, a base can also be added in order to accelerate the intramolecular Michael addition reaction. Here, the base includes DBU, DBN, LiH, NaH, KH, NaHMDS, Cs$_2$CO$_3$, K$_2$CO$_3$, imidazole, KO-t-Bu or a mixture thereof. Compound (IV) wherein $R_3$ is protected is subjected to oxidation at the 9-position in the same manner as in the above oxidation step, 11,12-cyclic carbamation, deprotection of the hydroxyl group at the 3-position, and then oxidation at the deprotected 3-position in the same manner as described above to obtain Compound (V).

EXAMPLES

Example 1

Preparation of Erythromycin A 11,12-cyclic Carbonate

To a solution of 150 g (0.20 mol) of erythromycin A in 0.5 L of toluene were added 75 g (0.54 mol) of potassium carbonate and 75 g (0.85 mol) of ethylene carbonate, and the resulting solution was stirred at 40° C. for 6 days. The solution was cooled, then to the reaction solution were added 0.2 L of toluene and 0.8 L of water, and the resulting solution was extracted. Then, the toluene layer was washed with a saturated aqueous sodium chloride solution and dried over anhydrous magnesium sulfate, and the solvent was evaporated under reduced pressure. The resulting residue was crystallized from ether to obtain 38.0 g of the title compound.

Example 2

Preparation of 9-deoxo-9-hydroxyerythromycin A 11,12-cyclic Carbonate

To a solution of 243 g (0.32 mol) of the compound obtained in Example 1 in 1 L of methanol was added 32.0 g of sodium borohydride under ice cooling. After 1 and 2 hours, sodium borohydride was further added thereto in portions of 30.0 g and 23.0 g, respectively. The resulting solution was stirred for 80 minutes, then the ice-bath was removed, and 500 mL of methanol and 17.3 g of sodium borohydride were added thereto (the total volume of sodium borohydride was 2.7 mol). The resulting solution was stirred for 40 minutes, then 4.5 L of ice water was added thereto, and the precipitate was collected by filtration. The precipitate was dissolved in 2.5 L of chloroform, and washed with a saturated aqueous sodium chloride solution. The washed solution was dried over anhydrous magnesium sulfate, and the solvent was evaporated under reduced pressure to obtain 232 g of the title compound.

Example 3

Preparation of 2'-O-acetyl-9-deoxo-9-hydroxyerythromycin A 11,12-cyclic Carbonate To a solution of 232 g (0.30 mol) of the compound obtained in Example 2 in 1.2 L of chloroform was added 34.1 g (0.33 mol) of acetic anhydride at room temperature. After having been stirred for 2 hours, the reaction solution was washed with a saturated aqueous sodium bicarbonate solution and water. Drying the organic layer over anhydrous magnesium sulfate and evaporating the solvent therefrom under reduced pressure gave 239 g of the title compound.

$^1$H NMR (500 MHz, CDCl$_3$) δ (ppm): 3.35 (s, 3H, 3"-O—CH$_3$), 3.39 (br, 1H, 9-H), 4.22 (dd, 1H, J=2.1, 5.8 Hz, 3-H), 4.61 (d, 1H, J=7.3 Hz, 1'-H), 4.80 (dd, 1H, J=7.6, 10.7 Hz, 2'-H)

ESI-MS: m/z=804.3 [M+H]$^+$

Example 4

Preparation of 2'-O-acetyl-6,9-O-acrylidene-9-deoxo-9-hydroxy-5-O-desosaminyl erythronolide A 11,12-cyclic Carbonate To a solution of 79.6 g (0.099 mol) of the compound obtained in Example 3 in 400 mL of toluene were added 53.8 g (0.41 mol) of acroleine diethyl acetal and 29.9 g (0.12 mol) of pyridinium p-toluenesulfonate. The resulting solution was refluxed with heating for 5 hours, and allowed to stand at room temperature overnight. The precipitate was collected by filtration and washed with 100 mL of toluene. The precipitate was added in a mixture of 500 mL of chloroform and 100 mL of a saturated aqueous sodium bicarbonate solution and dissolved while stirring. The chloroform layer was collected by separation, washed with a saturated aqueous sodium bicarbonate solution and water, and dried over anhydrous magnesium sulfate. Evaporation of the solvent therefrom under reduced pressure gave 54.2 g of the title compound.

$^1$H NMR (500 MHz, CDCl$_3$) δ (ppm): 3.80 (dd, 1H, J=4.0, 5.8 Hz, 9-H), 4.60 (d, 1H, J=7.3 Hz, 1'-H), 4.77 (dd, 1H, J=7.6, 10.7 Hz, 2'-H), 5.43 (d, 1H, J=5.5 Hz, >CH—CH=CH$_2$), 5.80 (ddd, 1H, J=4.9, 10.4, 17.1 Hz, >CH—CH=CH$_2$)

$^{13}$C NMR (125 MHz, CDCl$_3$) δ (ppm): 76.9 (3-C), 78.7 (6-C), 82.5 (9-C), 92.2 (>CH—CH=CH$_2$), 99.8 (1'-C), 115.8 (>CH—CH=CH$_2$)

ESI-MS: m/z=684.2 [M+H]$^+$

Example 5

Preparation of 6,9-O-acrylidene-9-deoxo-2',3-di-O-acetyl-9-hydroxy-5-O-desosaminyl erythronolide A 11,12-cyclic Carbonate To a solution of 54.2 g (0.079 mol) of the compound obtained in Example 4 in 271 mL of chloroform were added 16.1 g (0.16 mol) of triethylamine and 9.69 g (0.079 mol) of dimethylaminopyridine. Then 16.2 g (0.16 mol) of acetic anhydride was added to the resulting solution at room temperature, which was then stirred overnight. 8.12 g (0.08 mol) of acetic anhydride and 8.05 g (0.08 mol) of triethylamine were further added thereto and the resulting solution was stirred for 4.5 hours, and then washed with a saturated aqueous ammonium chloride solution, a saturated aqueous sodium bicarbonate solution and a saturated aqueous sodium chloride solution. The organic layer was dried over anhydrous magnesium sulfate, then the solvent was evaporated therefrom under reduced pressure. The concentrated residue was purified by a silica gel column chromatography (eluent; acetone:hexane:triethylamine=2:10:0.2), dissolved in 300 mL of toluene and washed with a saturated aqueous ammonium chloride solution, a saturated aqueous sodium bicarbonate solution and a saturated aqueous sodium chloride solution. The resulting solution was dried over anhydrous magnesium sulfate, then the solvent was evaporated under reduced pressure to obtain 35.2 g of the title compound.

$^1$H NMR (500 MHz, CDCl$_3$) δ (ppm): 2.08 (s, 3H, 2'-OAc), 2.15 (s, 3H, 3-OAc), 3.81 (dd, 1H, J=3.9, 6.0 Hz, 9-H), 4.18 (d, 1H, J=7.6 Hz, 1'-H), 5.43 (d, 1H, J=4.6 Hz, >CH—CH=CH$_2$), 5.83 (ddd, 1H, J=4.2, 10.3, 17.0 Hz, >CH—CH=CH$_2$)

$^{13}$C NMR (125 MHz, CDCl$_3$) δ (ppm): 77.7 (3-C), 78.5 (6-C), 82.4 (9-C), 91.9 (>CH—CH=CH$_2$), 100.4 (1'-C), 116.0 (>CH—CH=CH$_2$), 169.9 (3-OCO—CH$_3$)

ESI-MS: m/z=726.2 [M+H]$^+$

Example 6

Preparation of 9-deoxo-2',3-di-O-acetyl-9-hydroxy-6,9-O-(3-(3-quinolyl)acrylidene)-5-O-desosaminyl erythronolide A 11,12-cyclic Carbonate To a solution of 14.5 g (0.020 mol) of the compound obtained in Example 5 in 145 mL of tetrahydrofuran were added 6.24 g (0.030 mol) of 3-bromoquinoline, 9.67 g (0.030 mol) of tetrabutylammonium bromide and 7.76 g (0.060 mol) of diisopropylethylamine. After addition of 0.449 g (0.002 mol) of palladium acetate, the resulting solution was refluxed with heating under a nitrogen atmosphere for 7 hours. The solution was allowed to stand at room temperature overnight, then 0.449 g (0.002 mol) of palladium acetate was further added, and the resulting solution was refluxed with heating for 4 hours. The solution was allowed to stand for cooling, then the cooled solution was diluted with 500 mL of chloroform, washed with a saturated aqueous sodium bicarbonate solution and a saturated aqueous sodium chloride solution. The organic layer was dried over anhydrous magnesium sulfate, then the solvent was evaporated under reduced pressure. The concentrated residue was purified by a silica gel column chromatography (eluent; acetone:hexane:triethylamine= 2:10:0.2–5:10:0.2) to obtain 14.1 g of the title compound.

$^1$H NMR (500 MHz, CDCl$_3$) δ (ppm): 3.88 (dd, J=3.7, 6.1 Hz, 1H, 9-H), 4.21 (d, 1H, J=7.3 Hz, 1'-H), 5.70 (d, 1H, J=4.3 Hz, >CH—CH=CH—), 6.90 (d, 1H, J=16.5 Hz, =CH-quinolyl), 9.08 (d, 1H, J=2.4 Hz, 2-H of quinoline)

$^{13}$C NMR (125 MHz, CDCl$_3$) δ (ppm): 78.9 (6-C), 82.8 (9-C), 91.4 (>CH—CH=CH—), 100.5 (1'-C), 128.1 (=CH-quinolyl), 129.8 (3-C of quinoline)

ESI-MS: m/z=853.1 [M+H]$^+$

Example 7

Preparation of 9-deoxo-2',3-di-O-acetyl-9-hydroxy-6-O-((3-quinol-3-yl)prop-2-enyl)-5-O-desosaminyl erythronolide A 11,12-cyclic Carbonate To a solution of 2.56 g (3.0 mmol) of the compound obtained in Example 6 in 26 mL of nitrobenzene was added 1.05 g (9.0 mmol) of triethylsilane. Under nitrogen atmosphere, 2.0 mL (0.018 mol) of titanium tetrachloride was added thereto under ice-cooling. After 1.5 hours, the reaction solution was added to a mixture of 270 mL of chloroform and 200 mL of 5 mol/L aqueous sodium hydroxide solution while stirring. The precipitate was removed by filtration, and the organic layer was separated and washed with a saturated aqueous sodium chloride solution. The organic layer was dried over anhydrous magnesium sulfate, then the solvent was evaporated under reduced pressure. The concentrated residue was purified by a silica gel column chromatography (eluent; acetone:hexane:triethylamine=2:10:0.2–10:10:0.2) to obtain 1.89 g of the title compound.

$^1$H NMR (500 MHz, CDCl$_3$) δ (ppm): 0.99 (d, 3H, J=6.7 Hz, 8-CH$_3$), 3.30–3.42 (m, 2H, 5'-, 9-H), 4.13 (d, 1H, J=7.3 Hz, 1'-H), 4.24 (dd, 1H, J=7.3, 11.6 Hz, 6-OCH$_2$CH=CH—), 4.34 (dd, 1H, J=6.11, 11.6 Hz, 6-OCH$_2$CH=CH—), 9.08 (d, 1H, J=1.8 Hz, 2-H of quinoline)

$^{13}$C NMR (125 MHz, CDCl$_3$) δ (ppm): 64.6 (6-OCH$_2$CH=CH—), 79.3 (9-C), 80.3 (6-C), 100.8 (1'-C), 129.9 (3-C of quinoline), 131.0 (=CH-quinolyl)

ESI-MS: m/z=853.2 [M–H]$^-$

Example 8

Preparation of 2',3-di-O-acetyl-6-O-((3-quinol-3-yl)prop-2-enyl)-5-O-desosaminyl erythronolide A 11, 12-cyclic Carbonate To a solution of 1.71 g (2.0 mmol) of the compound obtained in Example 7 in 15.6 g (0.20 mol) of dimethyl sulfoxide was added 10.2 g (0.10 mol) of acetic anhydride at room temperature, followed by stirring for 6.5 hours. The reaction solution was soaked in an ice-bath, 100 mL of 5% aqueous ammonia was added. The precipitate was extracted with chloroform, and the extract was washed with a saturated aqueous sodium chloride solution. The organic layer was dried over anhydrous magnesium sulfate, then the solvent was evaporated under reduced pressure, and the concentrated residue was purified by a silica gel column chromatography (eluent; acetone:hexane:triethylamine=8:10:0.2) to obtain 1.65 g of the title compound.

$^1$H NMR (500 MHz, CDCl$_3$) δ (ppm): 1.14 (d, 3H, J=7.0 Hz, 8-CH$_3$), 3.01 (q, 1H, J=7.1 Hz, 10-H), 3.99 (dd, 1H, J=7.0, 11.3 Hz, 6-OCH$_2$CH=CH—), 4.04–4.12 (m, 2H, 6-OCH$_2$CH=CH—, 1'-H), 9.03 (d, 1H, J=2.2 Hz, 2-H of quinoline)

ESI-MS: m/z=853.1 [M+H]$^+$

Example 9

Preparation of 2',3-di-O-acetyl-10,11-anhydro-6-O-((3-quinol-3-yl)prop-2-enyl)-5-O-desosaminyl erythronolide A To a solution of 1.63 g (1.9 mmol) of the compound obtained in-Example 8 in 5 mL of dimethylformamide was added 0.66 g (5.7 mmol) of tetramethyguanidine. The resulting solution was stirred at 100° C. for 2 hours and diluted with 200 mL of chloroform. The diluted solution was washed with a saturated aqueous sodium chloride solution, dried over anhydrous magnesium sulfate, then the solvent was evaporated under reduced pressure. The concentrated residue was purified by a silica gel column chromatography (eluent; acetone:hexane:triethylamine=6:10:0.2) to obtain 1.55 g of the title compound.

ESI-MS: m/z 809.1[M+H]$^+$

Example 10

Preparation of 2',3-di-O-acetyl-6-O-((3-quinol-3-yl)prop-2-enyl)-5-O-desosaminyl erythronolide A 11, 12-cyclic Carbamate To a solution of 1.55 g (1.9 mmol) of the compound obtained in Example 9 in 8 mL of dimethylformamide was added 20 mL of tetrahydrofuran. To the resulting solution were added 1.24 g (7.6 mmol) of N,N-carbonyldiimidazole and 0.41 g (2.7 mmol) of 1,8-diazabicyclo[5.4.0]-7-undecene. The solution was allowed to stand at room temperature overnight, then ammonia gas was introduced therein at 0° C. for 4 hours then at 20° C. for 2 hours. Then 0.24 g (2.1 mmol) of potassium t-butoxide was added, and the resulting solution was stirred at room temperature overnight. 1 Mol/L hydrochloric acid was added to the solution to adjust to pH 6, then the resulting solution was extracted with isopropyl acetate and chloroform. The organic layer was washed with a saturated aqueous ammonium chloride solution, a saturated aqueous sodium bicarbonate solution and a saturated aqueous sodium chloride solution, in this order, and dried over anhydrous magnesium sulfate, and the solvent was evaporated under reduced pressure to obtain 1.46 g of the title compound.

ESI-MS: m/z=852.3[M+H]$^+$

Example 11

Preparation of 6-O-((3-quinol-3-yl)prop-2-enyl)-5-O-desosaminyl erythronolide A 11,12-cyclic Carbamate To a solution of 0.73 g (0.86 mmol) of the compound obtained in Example 10 in 10 mL of methanol was added 0.65 g (4.3 mmol) of 1,8-diazabicyclo[5.4.0]-7-undecene, and the resulting solution was refluxed with heating for 5 hours. The solvent was evaporated under reduced pressure, then the concentrated residue was dissolved in chloroform, and washed with a saturated aqueous ammonium chloride solution, a saturated aqueous sodium bicarbonate solution and a saturated aqueous sodium chloride solution, in this order. The organic layer was dried over anhydrous magnesium sulfate, then the solvent was evaporated under reduced pressure to obtain 0.58 g of the title compound.

ESI-MS: m/z=768.4[M+H]$^+$

Example 12

Preparation of 2'-O-propionyl-6-O-((3-quinol-3-yl)prop-2-enyl)-5-O-desosaminyl erythronolide A 11, 12-cyclic Carbamate To a solution of 0.56 g (0.73 mmol) of the compound obtained in Example 11 in 11 mL of chloroform was added 0.12 g (0.88 mmol) of propionic anhydride, and the resulting solution was stirred at room temperature for 2 hours. 0.12 g (0.88 mmol) of propionic anhydride was further added thereto, and the resulting solution was stirred for additional an hour. The reaction solution was diluted with 100 mL of chloroform, and washed with a saturated aqueous sodium bicarbonate solution and a saturated aqueous sodium chloride solution, in this order. The organic layer was dried over anhydrous magnesium sulfate, then the solvent was evaporated under reduced pressure. The concentrated residue was purified by a silica gel column chromatography (eluent; acetone:hexane:triethylamine=2:10:0.2–6:10:0.2) to obtain 0.45 g of the title compound.

ESI-MS: m/z=824.3[M+H]$^+$

Example 13

Preparation of 3-deoxy-3-oxo-2'-O-propionyl-6-O-((3-quinol-3-yl)prop-2-enyl)-5-O-desosaminyl erythronolide A 11,12-cyclic Carbamate To 1 mL of a dichloromethane solution of 83 mg of NCS and 54 µL of Me$_2$S was added dropwise at –10° C. 2 mL of a dichloromethane solution of 0.3 g of the compound obtained in Example 12, and the resulting solution was stirred for 45 minutes. To the reaction solution was added 0.12 mL of a solution of triethylamine in 0.5 mL of dichloromethane, and stirring was continued at –10° C. for further 3 hours. After working up in a similar manner to Example 6, purification of the concentrated residue by a silica gel column chromatography (eluent; chloroform:methanol:aqueous ammonia=20:1:0.1) gave 0.28 g of the title compound.

ESI-MS: m/z=844.4[M+Na]$^+$

Example 14

Preparation of 3-deoxy-3-oxo-6-O-((3-quinol-3-yl)prop-2-enyl)-5-O-desosaminyl erythronolide A 11, 12-cyclic Carbamate A solution of 0.2 g of the compound obtained in Example 13 in 5 mL of methanol was refluxed with heating for 2 hours. The methanol was evaporated under reduced pressure, and the residue was purified by a silica gel column chromatography (eluent; chloroform:methanol:aqueous ammonia=20:1:0.1) to give 0.16 g of the title compound, (the compound of Example 104 of U.S. Pat. No. 5,866,549).

ESI-MS: m/z=788.5[M+Na]$^+$

Example 15

Preparation of 2'-O-acetyl-9-deoxo-9-hydroxy-6,9-O-(3-(3-quinolyl)acrylidene)-5-O-desosaminyl erythronolide A 11,12-cyclic Carbonate To a solution of 54.6 g (0.080 mol) of the compound obtained in Example 4 in 273 mL of tetrahydrofuran were added 18.3 g (0.088 mol) of 3-bromoquinoline, 28.3 g (0.088 mol) of tetrabutylammonium bromide and 20.6 g (0.16 mol) of diisopropylethylamine. 1.79 g (8.0 mmol) of palladium acetate was added to the solution, which was then refluxed with heating for 8 hours. The solution was allowed to stand for cooling, then almost all of the solvent was evaporated under reduced pressure, and the residue was dissolved in 546 mL of chloroform and washed with 200 mL of 2 mol/L aqueous sodium hydroxide solution. The formed solid was removed off by filtration, and the organic layer was washed with a saturated aqueous sodium chloride solution and dried over anhydrous magnesium sulfate. Then the solvent was evaporated under reduced pressure, and the concentrated residue was purified by a silica gel column chromatography (eluent; acetone:hexane:triethylamine=3:10:0.2–6:10:0.2) to obtain 55.9 g of the title compound.

$^1$H NMR (500 MHz, CDCl$_3$) δ (ppm): 3.20–3.28 (m, 1H, 5'-H), 3.80–3.90 (m, 2H, 5-H & 9-H), 5.68 (d, 1H, J=4.3 Hz, >C$\underline{H}$—CH=CH—), 6.76 (d, 1H, J=15.9 Hz, =C$\underline{H}$-quinolyl), 8.97 (d, 1H, J=1.8 Hz, 2-H of quinoline)

$^{13}$C NMR (125 MHz, CDCl$_3$) δ (ppm): 76.0 (3-C), 79.0 (6-C), 82.7 (9-C), 90.9 (>$\underline{C}$H—CH=CH—), 99.7 (1'-C), 127.5 (=$\underline{C}$H-quinolyl), 129.8 (3-C of quinoline) ESI-MS: m/z=811.3 [M+H]+

Example 16

Preparation of 2'-O-acetyl-9-deoxo-9-hydroxy-6-O-((3-quinol-3-yl)prop-2-enyl)-5-O-desosaminyl erythronolide A 11,12-cyclic Carbonate To a solution of 45.7 g (0.056 mol) of the compound obtained in Example 15 in 457 mL of nitrobenzene was added 19.7 g (0.17 mol) of triethylsilane. Under nitrogen atmosphere, 37 mL (0.34 mol) of titanium tetrachloride was added to the solution dropwise under ice-cooling over 10 minutes. The resulting solution was stirred on an ice-bath for 10 minutes, then the ice-bath was removed, and the solution was stirred for additional 3 hours. Under ice-cooling, 500 mL of 2 mol/L aqueous sodium hydroxide solution was added to the solution. 1000 mL of chloroform was added thereto, stirring was continued for 30 minutes, and the solid was removed off by filtration. The organic layer was washed with a saturated aqueous sodium chloride solution and dried over anhydrous magnesium sulfate, and the solvent was evaporated under reduced pressure. The concentrated residue was purified by a silica gel column chromatography (eluent; acetone:hexane:triethylamine=2.5:10:0.2–6:10:0.2) to obtain 33.3 g of the title compound.

$^1$H NMR (500 MHz, CDCl$_3$) (ppm): 1.92–2.03 (m, 2H, 4-H & 10-H), 3.28–3.38 (m, 2H, 9-H & 5'-H), 4.04–4.20 (m, 3H, 3-OH & —O—C$\underline{H}_2$-vinyl), 6.73 (d, 1H, J=15.8 Hz, =C$\underline{H}$-quinolyl), 9.02 (d, 1H, J=2.1 Hz, 2-H of quinoline)

$^{13}$C NMR (125 MHz, CDCl$_3$) δ (ppm): 63.6 (6-O$\underline{C}$H$_2$CH=CH—), 76.6 (3-C), 79.6 (9-C), 80.6 (6-C), 100.0 (1'-C), 129.5 (3-C of quinoline), 130.4 (=$\underline{C}$H-quinolyl)

ESI-MS: m/z=813.3 [M+H]$^+$

Example 17

Preparation of 2'-O-acetyl-3-deoxy-3-oxo-6-O-((3-quinol-3-yl)prop-2-enyl)-5-O-desosaminyl erythronolide A 11,12-cyclic Carbonate To a solution of 1.63 g (2.0 mmol) of the compound obtained in Example 16 in 15.6 g (0.20 mol) of dimethyl sulfoxide was added 10.2 g (0.10 mol) of acetic anhydride at room temperature. The resulting solution was allowed to stand at room temperature overnight, and ice-cooled, then 100 mL of 5% aqueous ammonia was added thereto. The resulting solution was extracted with 200 mL of chloroform, and the extract was washed with a saturated aqueous sodium chloride solution. The organic layer was dried over anhydrous magnesium sulfate, then the solvent was evaporated under reduced pressure. The concentrated residue was purified by a silica gel column chromatography (eluent; acetone:hexane:triethylamine=4:10:0.2) to obtain 1.13 g of the title compound.

$^1$H NMR (500 MHz, CDCl$_3$) δ (ppm): 3.00 (q, 1H, J=6.7 Hz, 10-H), 3.18 (dq, 1H, J=4.9, 7.9 Hz, 4-H), 3.52–3.60 (m, 1H, 5'-H), 3.69 (dd, 1H, J=7.6, 11.3 Hz, 6-O—C$\underline{H}_2$—), 3.86–3.92 (m, 2H, 2-H & 6-O—C$\underline{H}_2$—), 6.58 (d, 1H, J=15.9 Hz, =C$\underline{H}$-quinolyl), 9.01 (d, 1H, J=2.5 Hz, 2-H of quinoline)

ESI-MS: m/z=809.2 [M+H]$^+$

Example 18

Preparation of 2'-O-acetyl-3-deoxy-3-oxo-6-O-((3-quinol-3-yl)prop-2-enyl)-5-O-desosaminyl erythronolide A 11,12-cyclic Carbamate To a solution of 0.809 g (1.0 mmol) of the compound obtained in Example 17 in 16 mL of tetrahydrofuran was added 0.350 g (2.3 mmol) of 1,8-diazabicyclo[5.4.0]-7-undecene, and the resulting solution was allowed to stand at room temperature for 4 days. 0.649 g (4.0 mmol) of carbonyl diimidazole was added to the solution, which was then stirred at room temperature for 70 minutes. The solution was then cooled in an ice-bath, and ammonia gas was introduced thereinto for 8 hours. The resulting solution was allowed to stand at room temperature overnight, then cooled in an ice-bath, and ammonia gas was introduced thereinto for 6.5 hours. The resulting solution was allowed to stand at room temperature overnight, then the reaction solution was diluted with 200 mL of toluene, washed with a saturated aqueous sodium chloride solution, and dried over anhydrous magnesium sulfate. The solvent was evaporated under reduced pressure. The concentrated residue was purified by a silica gel column chromatography (eluent; chloroform:methanol:28% aqueous ammonia=20:1:0.1) to obtain 0.405 g of the title compound.

ESI-MS: m/z=806.3[M−H]$^-$

Example 19

Preparation of 3-deoxy-3-oxo-6-O-((3-quinol-3-yl)prop-2-enyl)-5-O-desosaminyl erythronolide A 11,12-cyclic Carbamate A solution of 0.190 g (0.235 mmol) of the compound obtained in Example 18 in 4.8 mL of methanol was refluxed with heating for 3 hours. The solvent was evaporated under reduced pressure, then 2 mL of hexane was added, and the precipitated crystals were collected by filtration to obtain 0.148 g of the title compound.

Example 20

Preparation of 2'-O-acetyl-3-deoxy-3-oxo-6-O-((3-quinol-3-yl)prop-2-enyl)-5-O-desosaminyl erythronolide A 11,12-cyclic Carbonate 7.5 mL of a cooled (−18° C.) methylene chloride solution of 0.93 g (15 mmol) of dimethyl sulfide was added dropwise to 15 mL of a cooled (−18° C.) methylene chloride suspension of 1.60 g (12 mmol) of N-chlorosuccinimide, and the resulting mixture was stirred at −18° C. for 30 minutes. To the reaction solution was added dropwise −18° C. 15 mL of a methylene chloride solution of 2.44 g (3.0 mmol) of the compound obtained in Example 16, and the resulting solution was stirred for an hour. Next, 7.5 mL of a methylene chloride solution of 1.52 g (15 mmol) of triethylamine was added thereto dropwise at −18° C., while stirring was continued for additional 2 hours. To the reaction solution was added 50 g of ice, the resulting solution was extracted with 150 mL of chloroform, the extract was washed with a saturated aqueous sodium bicarbonate solution and a saturated aqueous sodium chloride solution. The extract was dried over anhydrous magnesium sulfate. The solvent was evaporated under reduced pressure, and the concentrated residue was purified by a silica gel column chromatography (eluent; acetone:hexane:triethylamine=4:10:0.2) to obtain 1.89 g of the title compound.

Example 21

Preparation of 2'-O-benzoyl-9-deoxo-9-hydroxyerythromycin A 11,12-cyclic Carbonate 1.00 g (1.31 mmol) of the compound obtained in Example 2 was dissolved in 50 mL of toluene and the solvent was evaporated under reduced pressure. The resulting residue was dissolved in 5 mL of tetrahydrofuran, and thereto were added 594 mg (2.63 mmol) of benzoic anhydride and 199 mg (1.97 mmol) of triethylamine. The resulting mixture was stirred at room temperature for 16 hours, 20 mL of ethyl acetate and 10 mL of purified water were added, and the mixture was stirred at room temperature for 10 minutes. After separating the mixture into layers, the aqueous layer was twice extracted with 20 mL portions of ethyl acetate. The combined organic layer was washed with 10% aqueous potassium dihydrogen phosphate solution, 10% aqueous sodium carbonate solution and saturated aqueous sodium chloride solution, dried over anhydrous magnesium sulfate, and filtered. The solvent was evaporated under reduced pressure. The residue was purified by silica gel column chromatography (eluent; acetone:hexane:triethylamine=2:10:0.2–5:10:0.2) to obtain 1.03 g of the title compound.

$^1$H NMR (500 MHz, CDCl$_3$) δ (ppm): 5.08(dd, 1H, J=10.4, 7.3 Hz, 2'-H), 7.43(t, 2H, J=7.6 Hz, aromatic proton), 7.55 (t, 1H, J=7.3 Hz, aromatic proton), 7.99–8.05 (m, 2H, aromatic proton)

$^{13}$C NMR(125 MHz, CDCl$_3$) δ (ppm): 128.2(aromatic carbon of benzoyl group), 129.7(aromatic carbon of benzoyl group), 130.7(aromatic carbon of benzoyl group), 132.6 (aromatic carbon of benzoyl group), 165.3 (2'-O—$\underline{C}$O—)

ESI-MS: m/z=888.5[M+Na]$^+$

Example 22

Preparation of 6,9-O-acrylidene-2'-O-benzoyl-9-deoxo-9-hydroxy-5-O-desosaminyl erythronolide A 11,12-cyclic Carbonate 10.0 g (11.5 mmol) of the compound obtained in Example 21 was dissolved in 150 mL of toluene and the solvent was evaporated under reduced pressure. The resulting residue was dissolved in 50 mL of toluene, and thereto were added 6.01 g (46.2 mmol) of acrolein diethyl acetal and 3.48 g (13.8 mmol) of pyridinium p-toluenesulfonate. The resulting mixture was refluxed with heating for 4.5 hours, and then allowed to cool and left to stand.

To the reaction solution were added 150 mL of ethyl acetate and 200 mL of 4 mol/L saturated aqueous sodium hydrogen carbonate solution. After separation into layers, the aqueous layer was twice extracted with 50 mL portions of ethyl acetate. The organic layers were combined, washed with 50 mL of saturated aqueous sodium chloride solution and dried over anhydrous magnesium sulfate. Evaporation of the solvent under reduced pressure gave a crude product. Purification of the concentrated residue by silica gel column chromatography (eluent; acetone:hexane:triethylamine=2:10:0.2–4:10:0.2) gave 5.94 g of the title compound.

$^1$H NMR (500 MHz, CDCl$_3$) δ (ppm): 5.10(s, 1H, 11-H), 5.25(d, 1H, J=17.1 Hz, >CH—CH=C$\underline{H}_2$), 5.41(d, 1H, J=4.9 Hz, >C$\underline{H}$—CH=CH$_2$), 5.79(m, 1H, >CH—C$\underline{H}$=CH$_2$)

$^{13}$C NMR(125 MHz, CDCl$_3$) δ (ppm): 92.2(>$\underline{C}$H—CH=CH$_2$), 115.8(>CH—CH=$\underline{C}$H$_2$), 136.3(>CH—$\underline{C}$H=CH$_2$)

ESI-MS: m/z=768.4[M+Na]$^+$

Example 23

Preparation of 2'-O-benzoyl-9-deoxo-9-hydroxy-6, 9-O-(3-(3-quinolyl)acrylidene)-5-O-desosaminyl erythronolide A 11,12-cyclic Carbonate 5.60 g (7.51 mmol) of the compound obtained in Example 22 was reacted in a similar manner to Example 15 to obtain 5.10 g of the title compound.

$^1$H NMR (500 MHz, CDCl$_3$) δ (ppm): 5.66(d, 1H, J=4.9 Hz, >CH—CH═CH—), 6.29(dd, 1H, J=15.9, 4.9 Hz, >CH—CH═CH-quinolyl), 6.72(d, 1H, J=15.9 Hz, ═CH-quinolyl), 8.98(d, 1H, J=1.8 Hz, 2-H of quinoline)

$^{13}$C NMR (125 MHZ, CDCl$_3$) δ (ppm): 79.0(6-C), 82.8 (9-C), 91.0(>CH—CH═CH—), 127.4(═CH-quinolyl), 129.9(>CH—CH═CH-quinolyl), 149.4(2-C of quinoline)

ESI-MS: m/z=895.3[M+Na]$^+$

Example 24

Preparation of 2'-O-benzoyl-9-deoxo-9-hydroxy-6-O-((3-quinol-3-yl)prop-2-enyl)-5-O-desosaminyl erythronolide A 11,12-cyclic Carbonate 1.49 g (1.71 mmol) of the compound obtained in Example 23 was reacted in a similar manner to Example 16 to obtain 790 mg of the title compound.

$^1$H NMR(500 MHz, CDCl$_3$) δ (ppm): 3.28(m, 1H, 9-H), 4.07–4.18(m, 2H, 6-O—CH$_2$CH═CH—), 6.50(m, 1H, 6-O—CH$_2$CH═CH—), 6.71(d, 1H, J=16.1 Hz, ═CH-quinolyl), 9.00(d, 1H, J=2.2 Hz, 2-H of quinoline)

$^{13}$C NMR(125 MHz, CDCl$_3$) δ (ppm): 63.6 (6-O—CH$_2$CH═CH—), 79.7(9-C), 80.7(6-C), 127.4(6-O—CH$_2$CH═CH—), 130.3(═CH-quinolyl), 149.4(2-C of quinoline) ESI-MS: m/z=897.4[M+Na]$^+$

Example 25

Preparation of 6,9-O-acrylidene-9-deoxo-9-hydroxy-5-O-desosaminyl erythronolide A 11,12-cyclic Carbonate 3.00 g (3.94 mmol) of the compound obtained in Example 2 was dissolved in 100 mL of toluene and the solvent was evaporated under reduced pressure. The resulting concentrated residue was dissolved in 30 mL of toluene, and thereto were added 2.05 g (15.7 mmol) of acrolein diethyl acetal and 1.19 g (4.74 mmol) of pyridinium p-toluenesulfonate. The mixture was refluxed with heating for one hour and 50 minutes, allowed to cool, and left to stand. 50 mL of ethyl acetate and 30 mL of 4 mol/L aqueous sodium hydroxide solution were added thereto. The resulting mixture was stirred at room temperature for 30 minutes and separated into layers, and the aqueous layer was twice extracted with 20 mL portions of ethyl acetate. The organic layers were combined, washed with saturated aqueous sodium chloride solution and dried over anhydrous magnesium sulfate. Evaporation of the solvent under reduced pressure gave a crude product. The concentrated residue was purified by silica gel column chromatography (eluent; chloroform:methanol:aqueous ammonia=30:1:0.1–10:1:0.1) to obtain 1.50 g of the title compound.

$^1$H NMR(500 MHz, CDCl$_3$) δ (ppm): 5.14 (d, 1H, J=10.4 Hz, >CH—CH═CH$_2$), 5.15(s, 1H, 11-H), 5.28(d, 1H, J=17.1 Hz, >CH—CH═CH$_{12}$), 5.45(d, 1H, J=4.9 Hz, >CH—CH═CH$_2$), 5.81(ddd, 1H, J=4.9, 10.4, 17.1 Hz, >CH—CH═CH$_2$)

$^{13}$C NMR(125 MHz, CDCl$_3$) δ (ppm): 78.6(6-C), 82.7(9-C), 91.8(>CH—CH═CH$_2$), 115.8(>CH—CH═CH$_2$), 136.2(>CH—CH═CH$_2$)

ESI-MS: m/z=642.3[M+H]$^+$

Example 26

Preparation of 9-deoxo-9-hydroxy-6-O-((3-quinol-3-yl)prop-2-enyl)-5-O-desosaminyl erythronolide A 11,12-cyclic Carbonate A solution of 93.5 g (0.115 mol) of the compound obtained in Example 16 in 500 mL of methanol was refluxed with heating for 4 hours. After allowing the resulting solution to cool, the solvent was evaporated under reduced pressure. Recrystallization of the resulting residue from ethyl acetate gave 70.6 g of the title compound.

$^1$H NMR (500 MHz, CDCl$_3$) δ (ppm): 3.17(d, 1H, J=5.5 Hz, 9-H), 3.25(dd, 1H, J=10.4, 7.3 Hz, 2'-H), 3.79(dd, 1H, J=9.8, 2.4 Hz, 3H), 9.01(d, 1H, J=1.8 Hz, 2-H of quinoline)

$^{13}$C NMR(125 MHz, CDCl$_3$) δ (ppm): 70.5(2'-C), 77.9 (3-C), 80.6(9-C), 81.2(6-C)

ESI-MS: m/z=771.4[M+H]$^+$

Example 27

Preparation of 2'-O-benzoyl-9-deoxo-9-hydroxy-6-O-((3-quinol-3-yl)prop-2-enyl)-5-O-desosaminyl erythronolide A 11,12-cyclic Carbonate 67.9 g (88.1 mmol) of the compound obtained in Example 26 was dissolved in 500 mL of toluene and the solvent was evaporated under reduced pressure. The residue was dissolved in 135 mL of tetrahydrofuran, and thereto was added 20.9 g (92.4 mmol) of benzoic anhydride. After stirring the mixture at 40–44° C. for 5.5 hours, 2.00 g (8.84 mmol) of benzoic anhydride was additionally added, and the resulting mixture was stirred with heating at the same temperature as above for 6 hours. To the reaction solution were added 34 mL of purified water and 13.0 g of potassium carbonate, and the resulting mixture was stirred with heating at 40–44° C. for 2 hours. After allowing the mixture to cool, 200 mL of ethyl acetate and 100 mL of purified water were added. The resulting mixture was separated into layers, and the aqueous layer was twice extracted with 100 mL portions of ethyl acetate. The organic layers were combined, washed with 4 mol/L aqueous sodium hydroxide solution and saturated aqueous sodium chloride solution, dried over anhydrous magnesium sulfate, and filtered. Evaporation of the solvent under reduced pressure gave 79.0 g of the title compound (the same compound as that obtained in Example 24).

Example 28

Preparation of 2'-O-benzoyl-3-deoxy-3-oxo-6-O-((3-quinol-3-yl)prop-2-enyl)-5-O-desosaminyl erythronolide A 11,12-cyclic Carbonate 78.8 g (90.0 mmol) of the compound obtained in Example 27 was reacted in a similar manner to Example 20 to obtain 71.7 g of the title compound.

$^1$H NMR(500 MHz, CDCl$_3$) δ (ppm): 2.72(m, 1H, 8-H), 3.06(m, 1H, 4-H), 3.77(q, 1H, J=6.7 Hz, 2-H)

$^{13}$C NMR(125 MHz, CDCl$_3$) δ (ppm): 168.6(1-C), 205.1 (3-C), 212.4(9-C)

ESI-MS: m/z=893.3[M+Na]$^+$

Example 29

Preparation of 10,11-anhydro-2'-O-benzoyl-3,11-dideoxy-3-oxo-6-O-((3-quinol-3-yl)prop-2-enyl)-5-O-desosaminyl erythronolide A To a solution of 20.0 g (23.0 mmol) of the compound obtained in Example 28 in 400 mL of tetrahydrofuran was added 15.9 g (0.115 mol) of anhydrous potassium carbonate. The resulting mixture was refluxed with heating for 23 hours. After allowing the reaction mixture to cool, the precipitate was filtered off and washed with 200 mL of ethyl acetate. The filtrate and washings thus obtained were washed with saturated aqueous sodium chloride solution, dried over anhydrous magnesium sulfate, and filtered. The solvent was evaporated under reduced pressure. Purification of the crude product thus obtained by silica gel column chromatography (eluent; acetone:hexane:triethylamine=3:10:0.2–5:10:0.2) gave 19.8 g of the title compound.

$^1$H NMR(500 MHz, CDCl$_3$) δ (ppm): 2.03(s, 3H, 10-Me), 4.97(dd, 1H, J=10.3, 2.6 Hz, 13-H), 5.07(dd, 1H, J=10.4, 7.6 Hz, 2'-H), 6.48(s, 1H, 11-H), 8.89(d, 1H, J=2.1 Hz, 2-H of quinoline)

$^{13}$C NMR(125 MHz, CDCl$_3$) δ (ppm): 73.5(12-C), 139.8 (10-C), 141.1(11-C), 208.3(3-C & 9-C)

ESI-MS: m/z=849.2[M+Na]$^+$

Example 30

Preparation of 10,11-anhydro-12-O-aminocarbonyl-2'-O-benzoyl-3,11-dideoxy-3-oxo-6-O-((3-quinol-3-yl)prop-2-enyl)-5-O-desosaminyl erythronolide A To a solution of 18.6 g (22.5 mmol) of the compound obtained in Example 29 in 372 mL of tetrahydrofuran were added 10.9 g (67.2 mmol) of carbonyldiimidazole and 342 mg (2.25 mmol) of 1,8-diazabicyclo[5.4.0]undec-7-ene. The resulting mixture was stirred for 3 hours with cooling. Then, under ice-cooling, ammonia gas was introduced into the mixture for 18.5 hours. After elevating the temperature, 400 mL of toluene and 100 mL of saturated aqueous sodium chloride solution were added, the resulting mixture was separated into layers, and the organic layer was twice washed with 100 mL portions of saturated aqueous sodium chloride solution, dried over anhydrous magnesium sulfate and filtered. Evaporation of the solvent under reduced pressure gave 20.2 g of the title compound.

$^1$H NMR(500 MHz, CDCl$_3$) δ (ppm): 1.90(s, 3H, 10-Me), 5.82(m, 1H, 13-H), 6.75(s, 1H, 11-H)

$^{13}$C NMR(125 MHz, CDCl$_3$) δ (ppm): 138.3(10-C), 141.1 (11-C), 154.4(12-O—$\underline{C}$O—NH$_2$)

ESI-MS: m/z=870.3[M+H]$^+$

Example 31

Preparation of 2'-O-benzoyl-3-deoxy-3-oxo-6-O-((3-quinol-3-yl)prop-2-enyl)-5-O-desosaminyl erythronolide A 11,12-cyclic Carbamate To a solution of 2.00 g (2.30 mmol) of the compound obtained in Example 30 in 20 mL of tetrahydrofuran was added 28.5 mg (0.230 mmol) of 1,5-diazabicyclo[4.3.0]non-5-ene. The resulting mixture was refluxed with heating for 27 hours. After allowing the mixture to cool, 50 mL of ethyl acetate and 30 mL of saturated aqueous sodium chloride solution were added to the mixture, the resulting mixture was separated into layers, and the aqueous layer was twice extracted with 20 mL portions of ethyl acetate. The organic layers were combined, washed with saturated aqueous sodium chloride solution, dried over anhydrous magnesium sulfate, and filtered. Then, the solvent was evaporated under reduced pressure. The resulting concentrated residue was three times purified by silica gel column chromatography (as the eluent, chloroform:methanol:aqueous ammonia= 30:1:0.1 was used once, and acetone:hexane:triethylamine= 3:10:0.2–5:10:0.2 was used twice) to obtain 1.53 g of the title compound (the same compound as that described in Example 10 of WO 0078773).

Example 32

Preparation of 2'-O-acetyl-9-deoxo-9-hydroxyerythromycin A 11,12-cyclic Carbonate Using ethyl acetate as a solvent, 0.762 g (1.00 mmol) of the compound obtained in Example 2 was reacted in a similar manner to Example 3. As a result, 0.74 g of the title compound (the same compound as that obtained in Example 3) was obtained.

Example 33

Preparation of 2'-O-acetyl-9-deoxo-9-hydroxy-6-O-((3-quinol-3-yl)prop-2-enyl)-5-O-desosaminyl erythronolide A 11,12-cyclic Carbonate To a solution of 4.87 g (6.01 mmol) of the compound obtained in Example 15 in 73 mL of nitrobenzene was added 0.811 g (6.97 mmol) of t-butyldimethylsilane. After replacing the atmosphere with nitrogen gas, the temperature was lowered to 5° C. Then, 4.1 mL (37.8 mmol) of titanium tetrachloride was dropwise added thereto over a period of 3 minutes. After stirring the resulting mixture for 40 minutes, the reaction solution was poured into a mixture of 35 mL of 28% aqueous ammonia and 60 g of ice. After stirring the resulting mixture for 30 minutes, the solid matter was filtered off and washed with 150 mL of toluene. The organic layer was washed three times with 50 mL portions of saturated aqueous sodium chloride solution. The toluene was evaporated under reduced pressure to obtain a yellow-brown colored solution containing the objective product. Under ice-cooling, 20 mL of 1 mol/L hydrochloric acid was added to the yellow-brown solution. After separating the resulting mixture into layers, the organic layer was extracted firstly with 10 mL of 1 mol/L hydrochloric acid and thereafter with 10 mL of water. The aqueous layers were combined and twice washed with 10 mL portions of toluene. The aqueous layer thus obtained was mixed with 0.50 g of active carbon (Norit "SX-II", manufactured by Wako Pure Chemical Industries, Ltd.), and stirred at room temperature for 16 hours. After filtering off the active carbon, 17.5 mL of a 2 mol/L aqueous sodium hydroxide solution was added under ice-cooling. The precipitate was 70 mL of dissolved in toluene, twice washed with 10 mL portions of saturated aqueous sodium chloride solution, dried over anhydrous magnesium sulfate, and concentrated under reduced pressure. As a result, 3.71 g of the title compound (the same compound as that obtained in Example 16) was obtained.

Example 34

Preparation of 2'-O-acetyl-6,9-O-acrylidene-9-deoxo-9-hydroxy-5-O-desosaminyl erythronolide A 11,12-cyclic Carbonate Tosylate 10.0 g (12.4 mmol) of the compound obtained in Example 3 was dissolved in 100 mL of chlorobenzene, and a 50 ml fraction of the solvent was evaporated under atmospheric pressure. Then, 6.53 g (50.2 mmol) of acrolein diethyl acetal and 3.75 g (14.9 mmol) of pyridinium p-toluenesulfonate were added. After refluxing the resulting mixture with heating for 5 hours, the mixture was allowed to stand overnight at room temperature. Then, the precipitate was collected by filtration and dried to obtain 7.15 g of the title compound.

¹H NMR(500 MHz, DMSO-d₆) δ (ppm): 2.06(s, 3H, 2'-OAc), 2.29(s, 3H, CH₃-Ph), 3.67(dd, 1H, J=5.5, 8.0 Hz, 9-H), 4.72(d, 1H, J=7.6 Hz, 1'-H), 5.48(d, 1H, J=5.5 Hz, >CH—CH=CH₂)

¹³C NMR(125 MHz, DMSO-d₆) δ (ppm): 20.7(CH₃—Ph), 75.0(3-C), 78.0(6-C), 82.1(9-C), 91.5(>CH—CH=CH₂), 98.0(1'-C), 115.3 (>CH—CH=CH₂), 169.7(2'-OCOCH₃)

ESI-MS: m/z=706.3[M+Na]⁺

Example 35

Preparation of 2'-O-acetyl-6,9-O-acrylidene-9-deoxo-9-hydroxy-5-O-desosaminyl erythronolide A 11,12-cyclic Carbonate Tosylate 5.00 g (6.18 mmol) of the compound obtained in Example 3 was dissolved in 50 mL of chlorobenzene, and a 25 mL fraction of the solvent was evaporated under the atmospheric pressure. Using 2.56 g (25.2 mmol) of acrolein dimethyl acetal in place of the acrolein diethyl acetal, a reaction was carried out in a similar manner to Example 34 to obtain 3.80 g of the title compound (the same compound as that obtained in Example 34).

Example 36

Preparation of 2'-O-acetyl-9-deoxo-9-hydroxy-6-O-((3-quinol-3-yl)prop-2-enyl)-5-O-desosaminyl erythronolide A 11,12-cyclic Carbonate 5.00 g (6.17 mmol) of the compound obtained in Example 15 was dissolved in 100 mL of nitrobenzene, and a 50 mL fraction of the solvent was evaporated under reduced pressure. Under water-cooling, a similar reaction to Example 16 was carried out by using 1.84 g (7.08 mmol) of triphenylsilane in place of the triethylsilane. As a result, 3.03 g of the title compound (the same compound as the compound obtained in Example 16) was obtained.

Example 37

Preparation of 2'-O-acetyl-3-deoxy-3-oxo-6-O-((3-quinol-3-yl)prop-2-enyl)-5-O-desosaminyl erythronolide A 11,12-cyclic Carbonate 0.70 g (5.50 mmol) of oxalyl chloride was dissolved in 7.5 mL of dichloromethane, and the atmosphere was replaced with nitrogen gas. After cooling the resulting solution on an acetone-dry ice bath, a solution of 0.859 g (11.0 mmol) of dimethyl sulfoxide in 2.5 mL of dichloromethane was dropwise added thereto. Then, a solution of 0.41 g (0.500 mmol) of the compound obtained in Example 16 in 2.5 mL of dichloromethane was dropwise added thereto, and the resulting mixture was stirred while cooled with acetone-dry ice. Then, 10.2 g (0.10 mmol) of triethylamine was added, and the resulting mixture was stirred while cooled with acetone-dry ice. Ice and toluene were added to the reacted mixture, and the temperature was elevated to room temperature. The organic layer was taken out and washed with saturated aqueous sodium hydrogen carbonate solution and saturated aqueous sodium chloride solution, and dried over anhydrous magnesium sulfate. Evaporation of the solvent under reduced pressure gave 0.39 g of the title compound (the same compound as the compound obtained in Example 17).

Example 38

Preparation of 2'-O-acetyl-9-deoxo-9-hydroxy-6,9-O-(3-(3-quinolyl)acrylidene)-5-O-desosaminyl erythronolide A 11,12-cyclic Carbonate A similar reaction to Example 15 was carried out in a toluene, using 0.50 g (0.62 mmol) of the compound obtained in Example 34, 0.14 g (0.68 mmol) of 3-bromoquinoline, 0.22 g (0.68 mmol) of tetrabutylammonium bromide, 0.24 g (1.85 mmol) of diisopropylethylamine and 13.8 mg of 10 mol % palladium acetate. Thus, 0.45 g of the title compound (the same compound as that obtained in Example 15) was obtained.

Example 39

Preparation of 2'-O-acetyl-6,9-O-acrylidene-9-deoxo-9-hydroxy-5-O-desosaminyl erythronolide A 11,12-cyclic Carbonate Tosylate 0.41 mL (4.35 mmol) of acetic anhydride was added to a solution of 3.02 g (3.96 mmol) of the compound obtained in Example 2 in 15 mL of chlorobenzene. The resulting mixture was stirred at room temperature for 2 hours. Subsequently, 2.43 mL (15.9 mmol) of acrolein diethyl acetal and 1.20 g (4.78 mmol) of pyridinium p-toluenesulfonate were added, and the resulting mixture was heated with stirring at 120° C. for 2.5 hours. Thereafter, the stirring was continued overnight at room temperature. The formed crystals were collected by filtration and washed with chlorotoluene. The crystal thus obtained was dried under reduced pressure at 60° C. for 2 hours to obtain 2.21 g of the title compound (the same compound as that obtained in Example 34).

Examples 40–49

Preparation of 2'-O-acetyl-9-deoxo-9-hydroxy-6-O-((3-quinol-3-yl)prop-2-enyl)-5-O-desosaminyl erythronolide A 11,12-cyclic Carbonate Reduction reaction of the compound obtained in Example 15 was carried out in a similar manner to Example 16 while varying the reaction solvent, to obtain the title compounds in the following yields.

| No. | Solvent used in the reaction | Yield (%) |
| --- | --- | --- |
| 40 | o-Nitrotoluene | 81.3 |
| 41 | Dichlorormethane | 73.1 |
| 42 | Chlorobenzene | 76.9 |
| 43 | Chlorotoluene | 67.2 |
| 44 | Fluorobenzene | 68.4 |
| 45 | o-Difluorobenzene | 55.1 |
| 46 | Xylene | 55.5 |
| 47 | Acetonitrile | 48.8 |
| 48 | Isopropyl ether | 29.2 |
| 49 | Chlorocyclohexane | 56.6 |

Advantageous Effects of the Invention

According to the present invention, a substituent can easily be introduced into the hydroxyl group at the 6-position of erythromycin A. The process according to the present invention makes it possible to advantageously synthesize 3-deoxy-3-oxo-6-O-((3-quinol-3-yl)prop-2-enyl)-5-O-desosaminyl erythronolide A 11,12-cyclic carbamate or the like.

What is claimed is:

1. A process for preparing Compound (V) defined below, which comprises the steps of:

(A) providing Compound (I) of the formula:

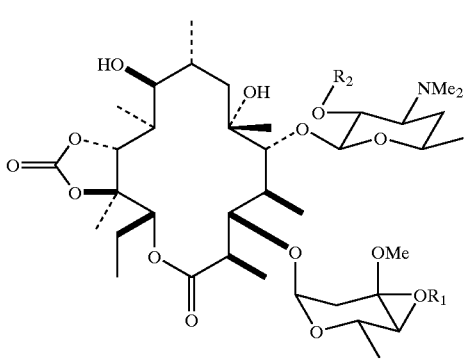

(I)

wherein R1 and R2, which may be the same or different, are a hydrogen atom, formula —CO—RA wherein RA is a C1–3 alkyl group, C1–3 alkyl group substituted with 1–3 halogen atoms, C1–3 alkoxy group, phenyl group, phenyloxy group, benzyloxy group, or phenyl group substituted with 1–3 substituents selected from the group consisting of C1–3 alkyl group, C1–3 alkoxy group, nitro group, cyano group, halogen atom, acetyl group, phenyl group and hydroxy group, or a silyl group substituted with 2–3 substituents selected from the group consisting of C1–4 alkyl group, phenyl group and benzyl group, by reaction of erythromycin with ethylene carbonate, subsequent reduction of ketone in 9-position, and optional protection of hydroxy groups in 2'- and/or 4"-positions, (B) reacting Compound (I) with a compound of the formula:

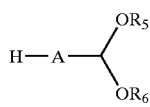

(1)

wherein A is CH=CH or C≡C; R5 and R6, which may be the same or different, are a C1–7 alkyl group, and optionally protecting a resulting 3-hydroxy group, to obtain Compound (II) of the formula:

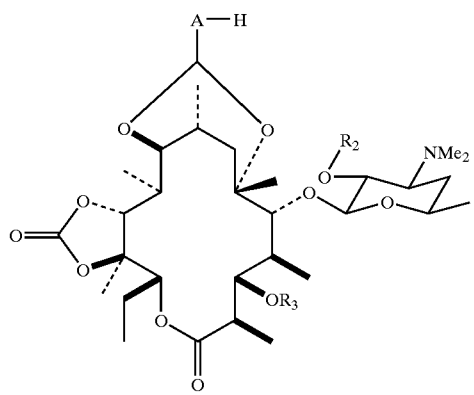

(II)

wherein R3 is the same as R1 defined above; R2 and A are as defined above, (C) reacting Compound (II) with a compound of the formula:

X—R4 (2)

wherein X is a halogen atom; R4 is the formula:

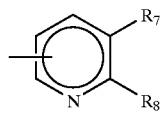

wherein R7 and R8 are a hydrogen atom or, alternatively, they form a benzene nucleus together with the adjacent carbon atoms, or the formula:

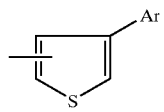

wherein Ar is a pyridyl group, quinolyl group or aryl group, to obtain Compound (III) of the formula:

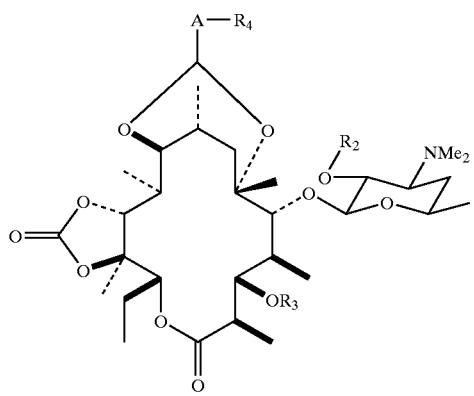

(III)

wherein A, R2, R3 and R4 are as defined above, (D) reacting Compound (III) with a compound of the formula:

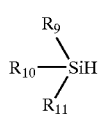

(3)

wherein R9 is a hydrogen atom, chlorine atom, linear or branched C1–4 alkyl group, C1–3 alkoxy group, phenyl or benzyl group; R10 and R11, which may be the same or different, are a chlorine atom, linear or branched C1–4 alkyl group, C1–3 alkoxy group, phenl group or benzyl group, to obtain Compound (IV) of the formula:

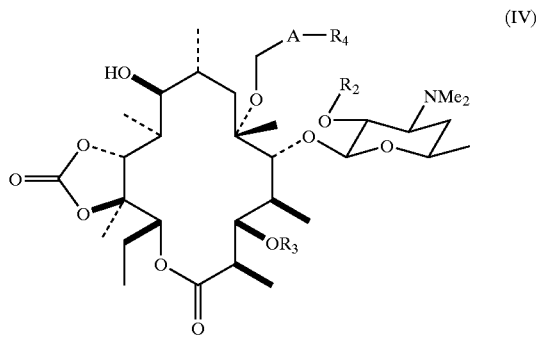

(IV)

wherein A, R2, R3 and R4 are as defined above, and (E) subjecting Compound (IV) to carbonylation at 9-position, carboxylation at 3-position, 11,12-cyclic carbamation and deprotection of 2'-hydroxy group, to obtain Compound (V) of the formula:

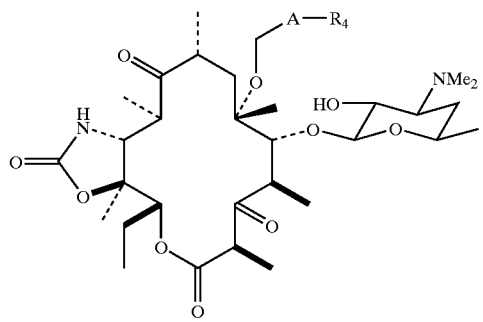

(V)

wherein A and R4 are as defined above.

2. The process according to claim 1 wherein the compound of formula (1) is selected from the group consisting of acrolein dimethyl acetal, acrolein diethyl acetal, acrolein di-n-propyl acetal, acrolein diisopropyl acetal, acrolein di-n-butyl acetal, acrolein diisobutyl acetal, propiolaldehyde dimethyl acetal, propiolaldehyde diethyl acetal, propiolaldehyde di-n-propyl acetal, propiolaldehyde diisopropyl acetal, propiolaldehyde di-n-butyl acetal and propiolaldehyde diisobutyl acetal.

3. The process according to claim 1 wherein the compound of formula (2) is selected from the group consisting of quinolyl chloride, pyridyl chloride, pyridylthienyl chloride, quinolyl bromide, pyridyl bromide and pyridylthienyl bromide.

4. The process according to claim 1 wherein the compound of formula (3) is selected from the group consisting of trimethylsilane, triethylsilane, trichlorosilane, phenyldimethylsilane, diphenylsilane, triphenylsilane, triethoxysilane, diethylsilane and t-butyldimethylsilane.

5. A compound of the formula:

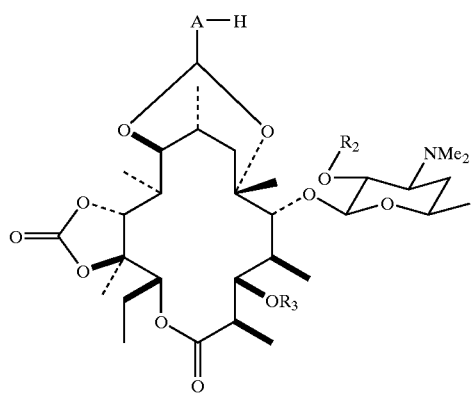

(II)

wherein A is CH=CH or C≡C; R2 and R3, which may be the same or different, are a hydrogen atom, formula —CO—RA wherein RA is a C1–3 alkyl group, C1–3 alkyl group substituted with 1–3 halogen atoms, C1–3 alkoxy group, phenyl group, phenyloxy group, benzyloxy group, or phenyl group substituted with 1–3 substituents selected from the group consisting of C1–3 lower alkyl group, C1–3 alkoxy group, nitro group, cyano group, halogen atom, acetyl group, phenyl group and hydroxy group, or a silyl group substituted with 2–3 substituents selected from the group consisting of C1–4 alkyl group, phenyl group and benzyl group.

6. A compound of the formula:

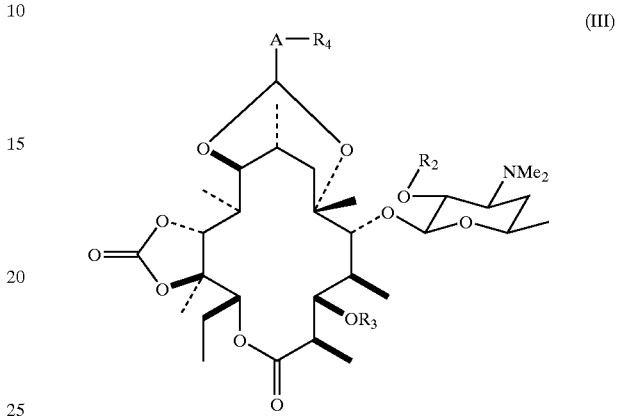

(III)

wherein A is CH=CH or C≡C; R2 and R3, which may be the same or different, are a hydrogen atom, formula —CO—RA wherein RA is a C1–3 alkyl group, C1–3 alkyl group substituted with 1–3 halogen atoms, C1–3 alkoxy group, phenyl group, phenyloxy group, benzyloxy group, or phenyl group substituted with 1–3 substituents selected from the group consisting of C1–3 lower alkyl group, C1–3 alkoxy group, nitro group, cyano group, halogen atom, acetyl group, phenyl group and hydroxy group, or a silyl group substituted with 2–3 substituents selected from the group consisting of C1–4 alkyl group, phenyl group and benzyl group; R4 is the formula:

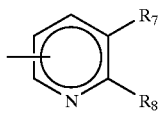

wherein R7 and R8 are a hydrogen atom or, alternatively, they form a benzene nucleus together with adjacent carbon atoms, or the formula:

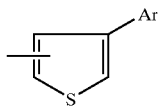

wherein Ar is a pyridyl group, quinolyl group or aryl group.

7. A process for preparing a decladinosylated 6,9-cyclic acetal erythromycin derivative defined below, which comprises the step of reacting Compound (I) of the formula:

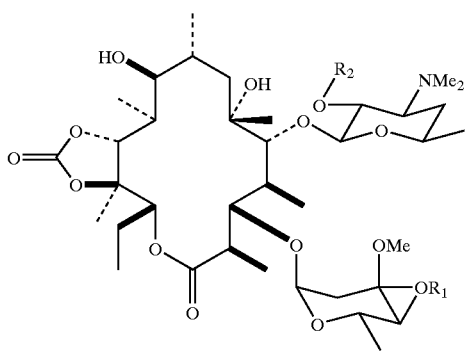

(I)

(1)

wherein A is CH=CH or C≡C; R5 and R6, which may be the same or different, are a C1–7 alkyl group, to obtain the decladinosylated 6,9-cyclic acetal erythromycin derivative of the formula:

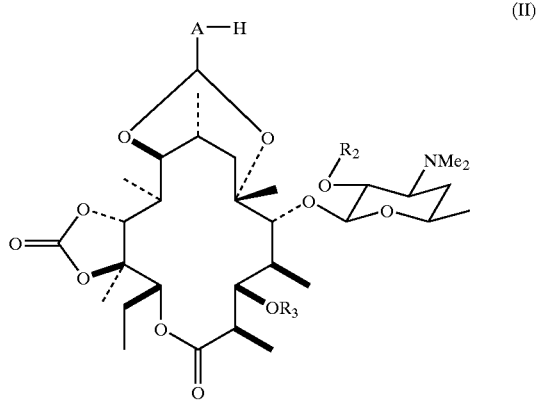

(II)

wherein R1 and R2, which may be the same or different, are a hydrogen atom, residue —CO—RA in which RA is a C1–3 alkyl group, C1–3 alkyl group substituted with 1–3 halogen atoms, C1–3 alkoxy group, phenyl group, phenyloxy group, benzyloxy group, or phenyl group substituted with 1–3 substituents selected from the group consisting of C1–3 alkyl group, C1–3 alkoxy group, nitro group, cyano group, halogen atom, acetyl group, phenyl group and hydroxy group, or a silyl group substituted with 2–3 substituents selected from the group consisting of C1–4 alkyl group, phenyl group and benzyl group, with a compound of the formula:

wherein R3 is the same as R1 defined above; R2 and A are as defined above.

* * * * *